United States Patent [19]

Austin et al.

[11] 4,108,552

[45] Aug. 22, 1978

[54] METHOD AND SYSTEM FOR DETECTING ULTRA-TRACE QUANTITIES OF METAL CARBONYLS

[75] Inventors: Terry Marshall Austin; Eugene Thomas Carroll, both of St. Albans; Mildred Choi Bowen, Charleston, all of W. Va.

[73] Assignee: Union Carbide Corporation, New York, N.Y.

[21] Appl. No.: 700,842

[22] Filed: Jun. 29, 1976

[51] Int. Cl.² .............................................. G01V 3/30
[52] U.S. Cl. ...................................... 356/87; 356/187
[58] Field of Search .......................... 356/87, 187, 72; 23/254 EF

[56] References Cited

U.S. PATENT DOCUMENTS 3,234,779  2/1966  Dawson, Jr. .......................... 73/23.1
3,489,498  1/1970  Brody et al. ......................... 356/187

OTHER PUBLICATIONS

Gaydon, A. G. "The Spectroscopy of Flames", John Wiley & Sons 1957, pp. 223–233.
Degent et al. "Contribution to the Study of the Formation, Elimination & Analysis of Traces of Iron Carbonyl & Nickel Carbonyl in the Gas of the Beynes Underground Reservoir" Compte Rendu Assoc. Tech. de L'Ind. du Gaz; pp. 478-501, 1961, French Report.

Primary Examiner—John K. Corbin
Assistant Examiner—Wm. H. Punter
Attorney, Agent, or Firm—Eugene Lieberstein

[57] ABSTRACT

A fluid matrix is sampled and evaluated for the presence of a metal carbonyl by separating predetermined elemental components from one another, forming an admixture between such elements and a carrier gas, oxidizing the admixture in the presence of an oxygen rich flame, selecting a predetermined range of wavelengths from the emission spectrum generated by the oxidized admixture and detecting the selected range.

14 Claims, 12 Drawing Figures

METHOD AND SYSTEM FOR DETECTING ULTRA-TRACE QUANTITIES OF METAL CARBONYLS

This invention relates to a method and system for detecting the presence of ultra trace quantities of metal carbonyls in a fluid matrix and for measuring the ultra trace level of each carbonyl constituent within the matrix.

It is presently known that metal carbonyls, particularly iron pentacarbonyl $Fe(CO)_5$ and nickel tetracarbonyl $Ni(CO)_4$ function as catalyst poisons in the processing of synthesis gas containing compositions of hydrogen and carbon monoxide, even at concentration levels of only low parts per billion on a volume per volume basis. Metal carbonyls are also known to be highly toxic to human personnel. In fact, minimum hygienic standards limit iron pentacarbonyl to a threshold level of only 10 parts per billion and nickel tetracarbonyl to only 1 part per billion respectively. Accordingly, it may be necessary to detect and monitor the concentration level of metal carbonyls in the raw material fuel supply of certain chemical processes particularly processes using fluid compositions containing carbon monoxide, and it would be desirable to monitor for the presence of toxic metal carbonyls in certain atmospheric environments.

Known analytical detection techniques may be classified as direct or indirect. The indirect category primarily relates to laboratory oriented processes employing pretreatment of the sample containing the trace contaminant in order to enhance the concentration of the trace element under examination. This procedure is by its very nature discontinuous and time consuming. Conversely, direct analysis lends itself to a relatively continuous mode of measurement which is much faster and which is oriented toward on line process treatment. Heretofore, detection of ultra trace levels of metal carbonyls has been limited to the indirect detection technique. =Ultra trace levels" are defined for purposes of the present specification as being below at least about one part per million and preferably below 50 parts per billion on a volume per volume basis. Commercially available direct detection systems such as flameless atomic absorption, fourier transform spectroscopy, and plasma chromatography have been investigated and found unreliable for measurement of metal carbonyls at the low ultra trace levels of interest. These direct detection systems suffer primarily from an inability to prevent interference from other fluid matrix materials and are unable to discriminate between different metal carbonyls present in the fluid matrix. The ability to discriminate between metal carbonyls is essential for quantitative measurement of each of the carbonyls present in the fluid matrix. Once the individual carbonyls present have been distinguished and their relative magnitudes established, separate measures may be taken to eliminate or suppress any or all of the identified carbonyls to the extent necessary to meet hygienic standards and/or to restore the chemical process to its viable condition of operation.

The accurate detection of ultra trace levels of metal carbonyls requires not only a technique which is sensitive but also highly selective to the presence of predetermined metal carbonyls without suffering from interference and masking from other components including other unknown trace contaminants in the fluid matrix.

It is, accordingly, the principal object of the present invention to provide a method and system for the direct detection of metal carbonyls within a fluid matrix.

Further objects and advantages of the present invention will become apparent from the following detailed description of the present invention when read in connection with the accompanying drawings of which:

Figure 1:
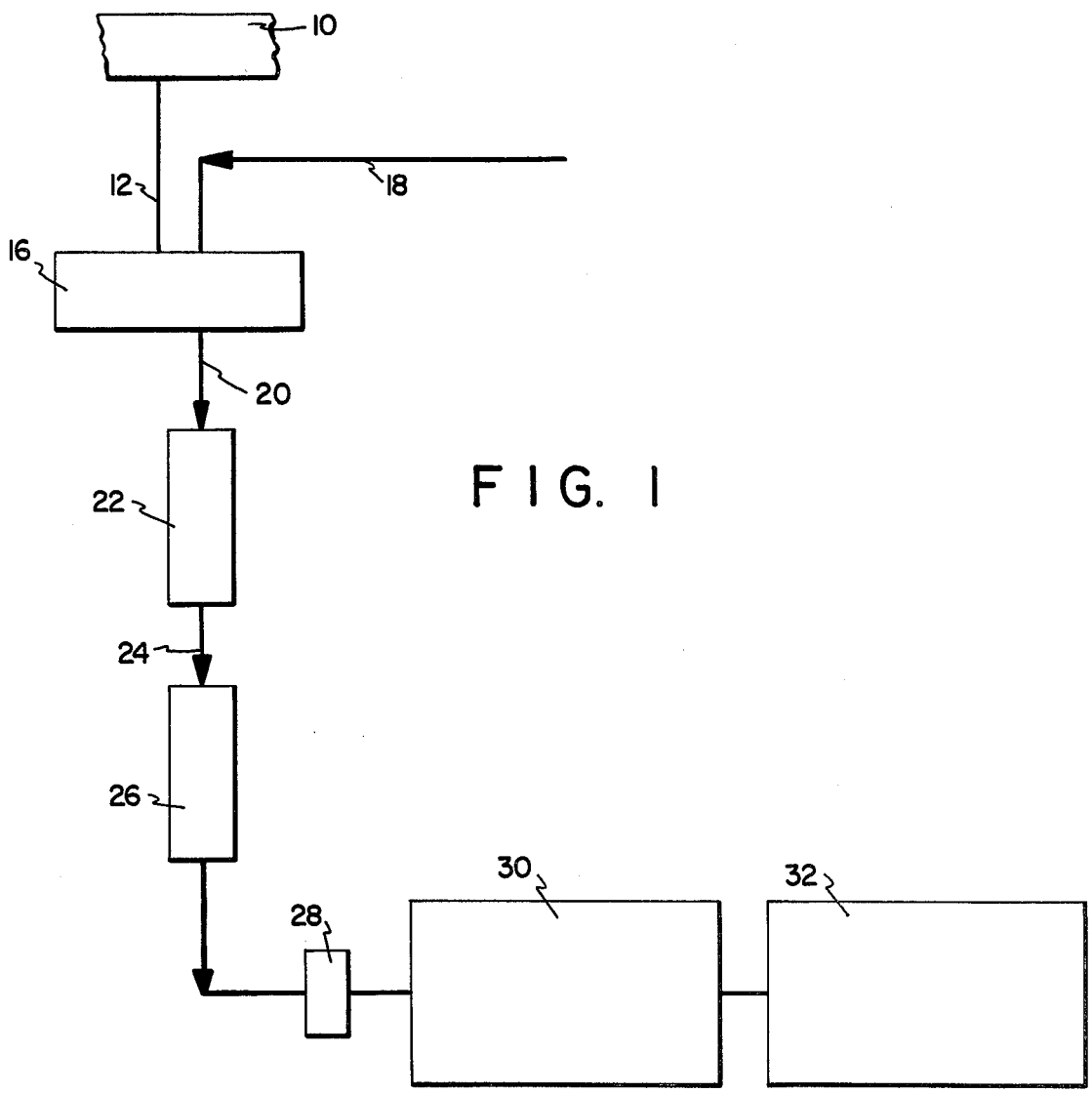
FIG. 1 is a schematic diagram of the metal carbonyl detection system of the present invention.

Now referring particularly to FIG. 1 in which a fluid sample 12 is taken from a fluid matrix 10 and analyzed in accordance with the method and system of the present invention for the existence of a predetermined metal carbonyl at ultra trace concentration levels. The fluid matrix 10 may represent any multi-component fluid such as a predetermined atmosphere or may represent a body or stream of any such fluid at any stage within any given chemical process. Moreover, although the fluid matrix 10 need not be in a gaseous state during sampling, conversion of the fluid sample 12 to a gaseous vapor would be necessary for detection of the trace element under examination.

The injection of a predetermined measure of fluid sample 12 into the carrier stream 18 is performed by the sample injector 16 which is a conventional valve mechanism constructed of predetermined materials compatible with the sample components under investigation. The combined effluent from the sample injector 16 is passed through line 20 into a component separator 22 which separates predetermined components of the fluid sample 12 from one another. The output of the component separator 22 is a series of binary admixtures of the fluid carrier 18 in combination with each of the separated components of the fluid sample 12. The output of the component separator 22 is fed through line 24 into the emission source 26 which generates a molecular wavelength emission spectrum for each of the binary admixtures presented to the source. A predetermined narrow band of wavelengths is selected from the emission spectrum by means of the optical wavelength selector 28. Thereafter, the trace metal carbonyl under examination is electro-optically detected by detector 30 using a conventional photomultiplier for example and recorded using a conventional electrical signal recorder 32 from which the concentration of the subject trace contaminant may be readily ascertained.

The carrier gas 18 may be any individual gas or composition which will not chemically react with the fluid sample 12 and which has a low level emission spectrum characteristic within the narrow band of wavelengths selected by the optical wavelength selector 28. Inert gases such as helium and nitrogen, etc. as well as hydrogen, carbon dioxide and carbon monoxide are suitable for use as the carrier gas 18. The flow rate of the carrier gas 18 through the component separator 22 is an important consideration for achieving desirable displacement of the individual components of the injected measure of fluid sample 12 in the component separator 22. A carrier flow rate range of between 15-150 milliliters per minute has been found satisfactory. The measure of fluid sample 12 injected into the carrier gas 18 will vary with the carbonyl constituent under examination but should lie in a range of between 10-100 cubic centimeters. Moreover, although any conventional gas injecting mechanism 16 may be used for introducing the controlled measure of fluid sample 12 into the stream of carrier gas 18 it is essential that the passageways in contact with the flowing gases be constructed or lined with a material which will not contaminate the sample fluid 12. Plastic materials such a polypropylene or Teflon a polymer of TFE tetrafluoroethylene or fluoronated ethylene propylene are preferred for this purpose. The sample injector 16 may be either pneumatically or electrically actuated in a conventional manner and at controlled intervals of time sufficient to allow for complete resolution of the predetermined fluid components in the component separator 22.

The component separator 22 is preferably a conventional gas chromatographic column which is packed with a material which will provide a different absorption affinity to each component of the fluid sample 12. Accordingly, the elution time for each of the components in the fluid sample will be different. The packing material in the chromatographic column is preferably a solid material such as, for example, chromasorb P coated with triethylhexylorthosilicate. The column material may be either nonpolar or of high or low polarity and may be of open tubular construction or may be a capillary column. Although separation through a chromatographic column is preferred other known component separating techniques are within the contemplation of the present invention including wet chemical separation and membrane diffusion.

The binary admixtures from the component separator 22 are supplied through line 24 to the emission source 26 which may represent any conventional excitation source capable of exciting the oxidized molecules within the admixture to luminescence so as to generate a molecular emission spectrum for the subject trace contaminant. The preferred excitation source 26 is a conventional flame cell. It has, however, been discovered in accordance with the present invention that to obtain a detectable electromagnetic radiation spectrum for the ultra trace levels of metal carbonyls in the flame cell the influent stream must be burned in an oxygen rich flame. An "oxygen rich flame" is defined for purposes of the present invention as being any flame in which the amount of oxidant is in excess of the stoichiometric quantity required for complete combustion. The preferred flame is a fuel air or fuel oxygen flame preferably of hydrogen and air in a preferred ratio of at least about one part fuel to three parts air. When iron pentacarbonyl and nickel tetracarbonyl are introduced into an oxygen rich flame both compounds are oxidized to form the transient molecules FeO and NiO, respectively. The oxidized molecules are elevated during their formation into excited electronic states. Subsequent decay of the excited electronic states give rise to an electromagnetic spectrum in the visible region. There is also an ultra violet emission occurring when iron carbonyl is introduced into the oxygen rich flame due to the formation of excited FeOH.

In accordance with the present invention it has also been found to be preferable to isolate a narrow and predetermined region within the ultra-violet and visible light region of the emitted electromagnetic radiation spectrum. Accordingly, the optical wavelength selector 28, which is preferably an interference filter, should have a bandwidth which transmits in a preferred range from between about 350 to 625 nanometers with a wavelength transmission peak in either a first range of between 350 to 400 nanometers or in a second or more preferred range of between 500 to 600 nanometers. Moreover, the filter 28 should preferably have a limited bandwidth of no greater than about 100 nanometers depending upon how accurate the measurement must be.

Figure 2:
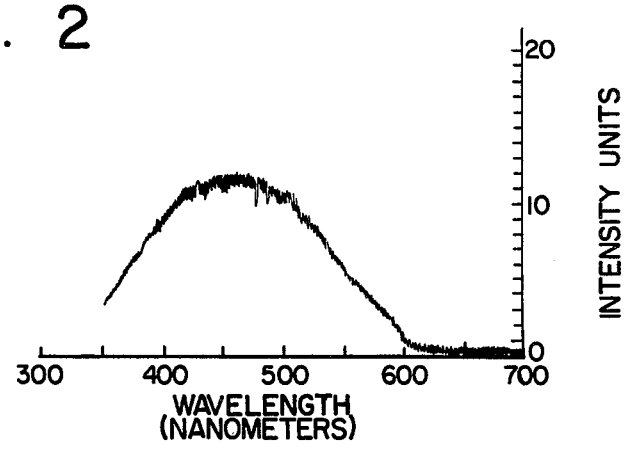
FIG. 2 is a recorded spectrogram of the emission spectra of an essentially 100% carbon monoxide sample burning in an air hydrogen flame.
Figure 3:
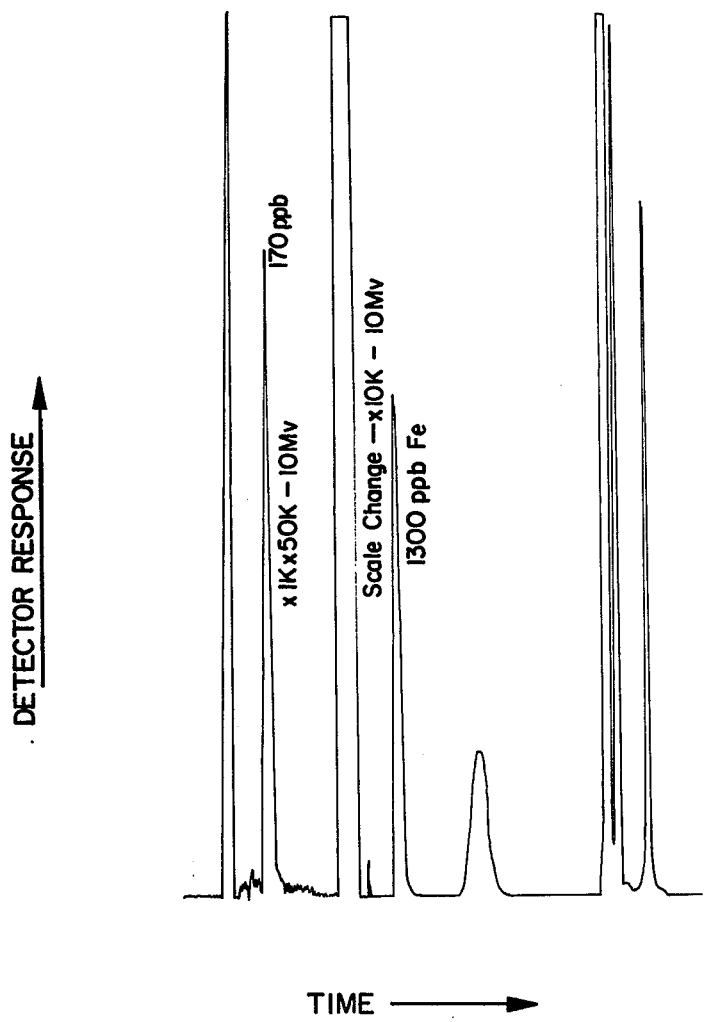
FIG. 3 is a chromatographic recording in accordance with the present invention of the spectral emission from a further sample of essentially 100% carbon monoxide derived from a common source of supply from which the sample of FIG. 2 was obtained.

A spectrogram of a sample of essentially 100% carbon monoxide is shown in FIG. 2. As is apparent from the Figure there is no discernible emission structure, only a broad band continuous emission resulting from the oxidation of carbon monoxide. The spectrogram was taken using a conventional scanning spectrophotometric apparatus. The sample was supplied from a cylinder of a commercially distributed research grade of carbon monoxide. A further sample from the same source of commercial 100% carbon monoxide was investigated using the method of the present invention to detect the presence of any metal carbonyl particularly a nickel and/or iron carbonyl in the sample. The sample was shown to contain as illustrated in FIG. 3, 1.3 parts per million iron pentacarbonyl and 170 parts per billion nickel tetracarbonyl respectively.

Figure 4:
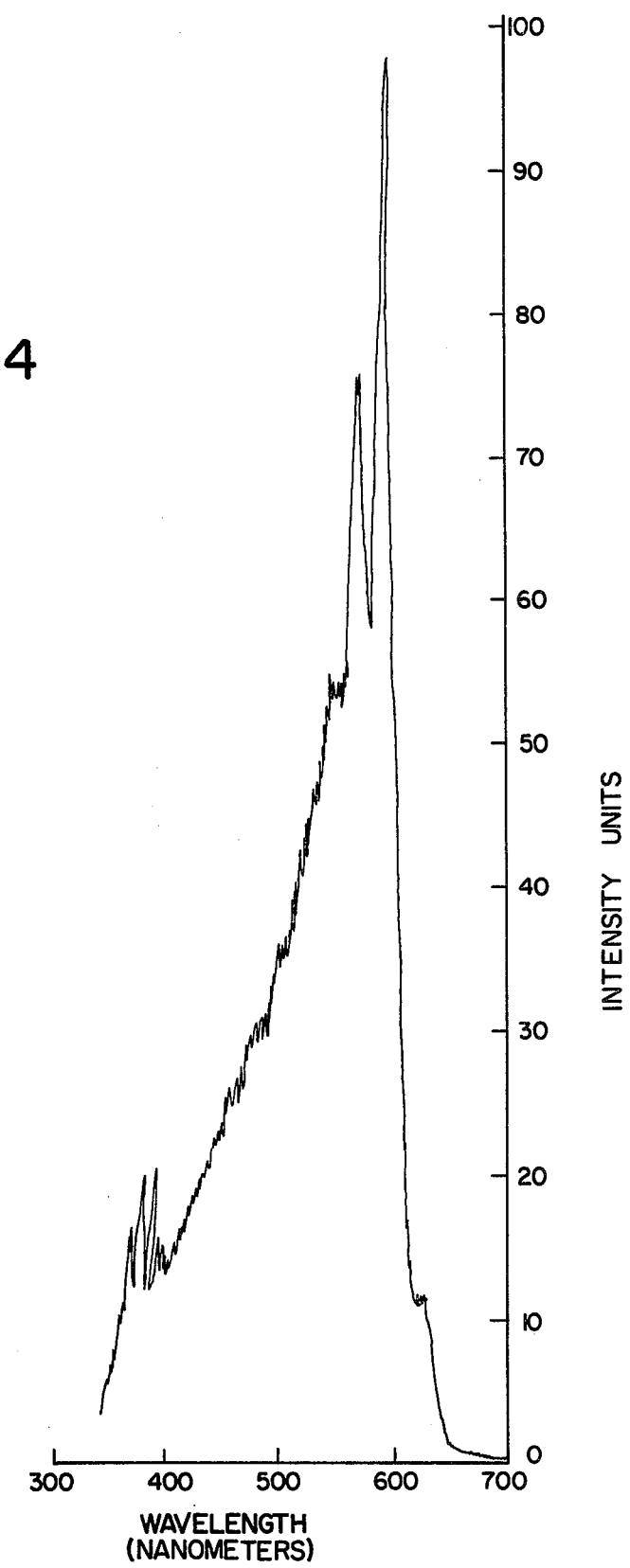
FIG. 4 is a recorded spectrogram of the emission spectra of a predetermined sample of iron pentacarbonyl in a controlled fluid matrix of hydrogen and carbon monoxide.
Figure 5:
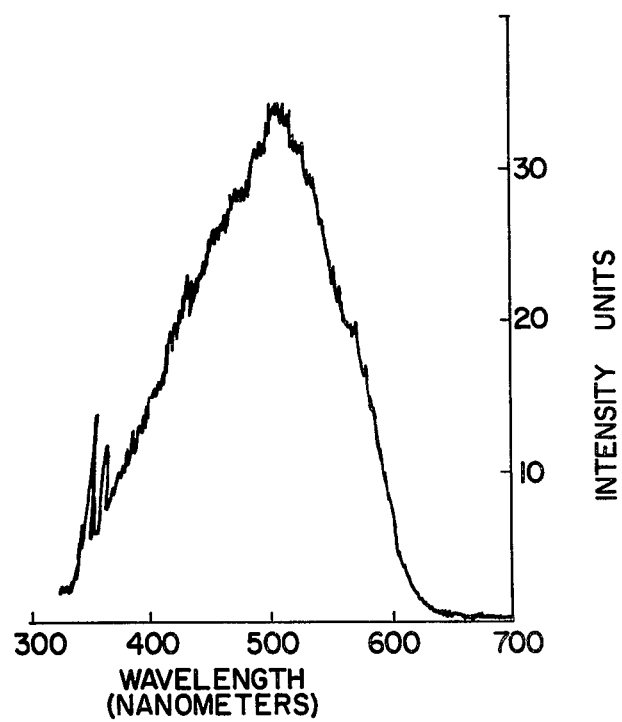
FIG. 5 is a recorded spectrogram of the emission spectra of a predetermined sample of nickel tetracarbonyl in a controlled fluid matrix of hydrogen and carbon monoxide equivalent to that of FIG. 4.

The spectrograms of FIGS. 4 and 5 provide the basis for determining the optimum spectral regions to be examined when detecting iron and nickel carbonyl respectively. The emission spectra in FIG. 4 was taken for a predetermined sample gas containing 25 parts per million of iron pentacarbonyl $Fe(CO)_5$ in a 50:50 mixture of hydrogen and carbon monoxide. A similar sample gas containing 25 parts per million of nickel tetracarbonyl in a 50:50 mixture of hydrogen and carbon monoxide was used for the recorded spectrograph of FIG. 5. It should be understood that the 25 parts per million of carbonyl concentration in the sample is orders of magnitude above the ultra trace levels of interest. Ultra trace carbonyl concentrations will not provide a spectrographic recording in which the carbonyl emission is distinguishable from the background continuum. Nonetheless, the spectogram of FIG. 4 is useful in that it indicates spectral peaks between 350 and 400 nanometers and between 500–600 nanometers which must be primarily attributable to the presence of the iron carbonyl component in the sample notwithstanding the interference from carbon monoxide whereas in FIG. 5 successive spectral peaks appear only in the region of 350 to 400 nanometers due to the presence of the nickel carbonyl component. Although this would appear to give a preference to the near ultra-violet to the visible region lying between 350 to 400 nanometers the visible region of between 500–600 nanometers has proved to be more sensitive in distinguishing between ultra trace levels of multiple metal carbonyls particularly nickel and iron and especially at very low detection levels of less than 10 parts per billion.

Figure 6:
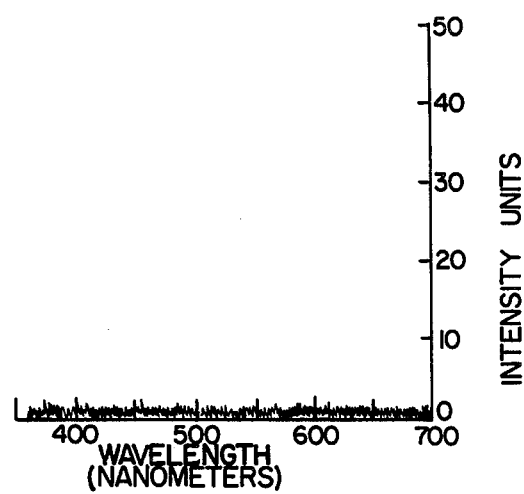
FIG. 6 is a recorded spectrogram of the emission spectra of an essentially 100% hydrogen sample burning in an air hydrogen flame.

A recorded spectrogram of a sample of essentially 100% hydrogen is illustrated in FIG. 6. The recording shows a very low level emission response of only nominal intensity throughout the entire spectral region of interest. Hence, for fluid matrices including compositions of hydrogen and carbon monoxide known as synthesis gas, the influence from the hydrogen component will be negligible and may be ignored in testing for the presence of one or more metal carbonyls.

Figure 7:
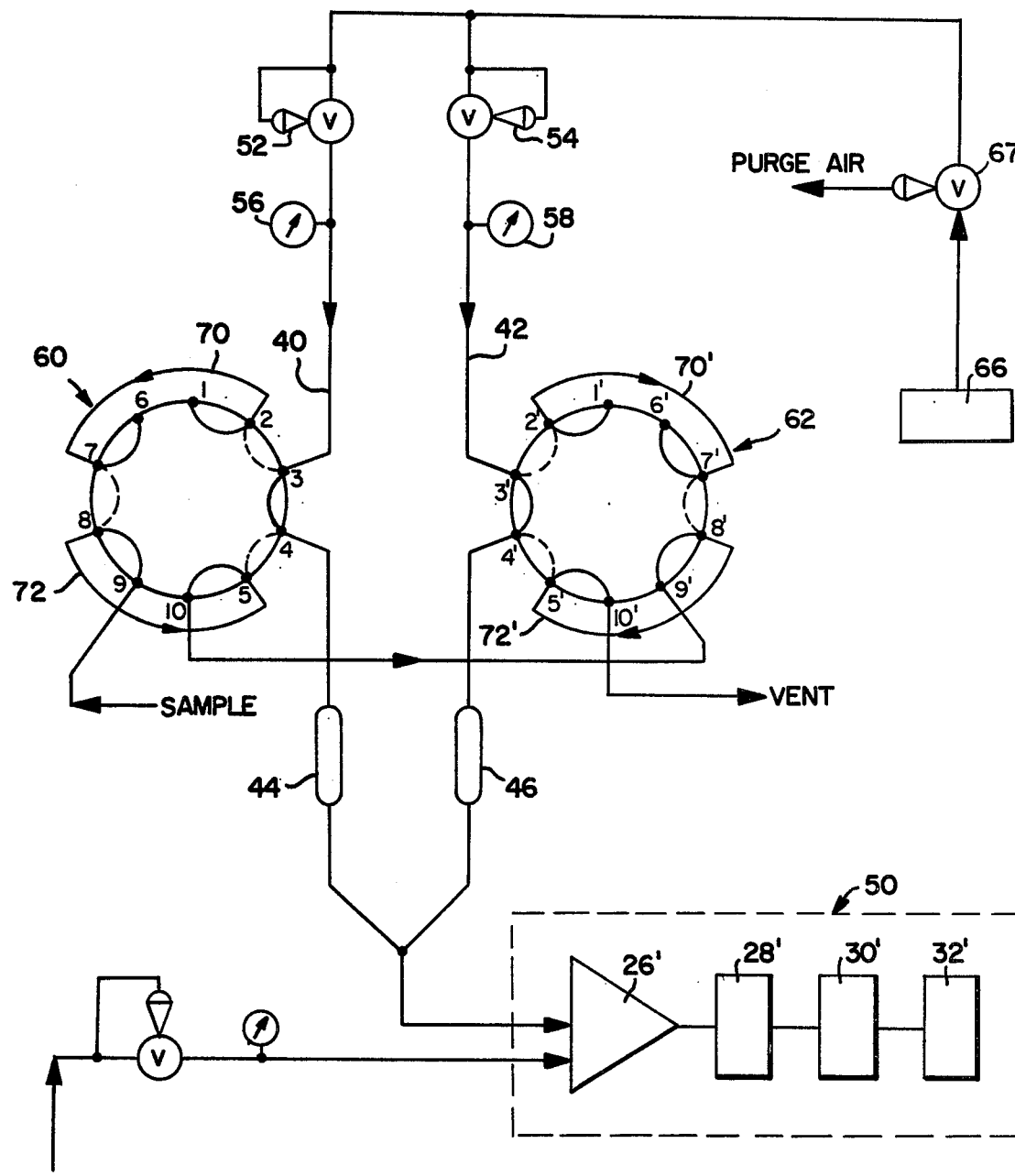
FIG. 7 is a modified schematic diagram of FIG. 1 for the combined detection of nickel tetracarbonyl and iron pentacarbonyl in accordance with the present invention.

The preferred system for detecting and distinguishing between nickel tetracarbonyl and iron pentacarbonyl in any fluid matrix medium and at levels down to one part per billion or less with a relatively high degree of resolution and accuracy is shown in FIG. 7. The system includes two carrier supply lines 40 and 42 which are substantially identical to one another and to their counterpart in FIG. 1. The carrier supply line 40, however, includes a component separator 44 which separates iron pentacarbonyl into an admixture with the carrier gas whereas the carrier line 42 includes a component separator 46 which separates nickel tetracarbonyl into an admixture with the carrier gas. Each carrier supply line 40 and 42 further includes a pressure regulator 52, 54, a pressure gauge 56, 58 and a sample injector 60 and 62 respectively. Each of the component separators 44 and 46 represent a chromatographic column of equal dimensions as follows: ⅛ inch outside diameter; 0.080 inside diameter; 48 inches length. It is not necessary for the component separators to be equal in dimension and in fact, their dimensions may vary substantially from one another. The packing material in each column 44 and 46 consists of chromasorb P coated with triethylhexylorthosilicate. A 5% coating of triethylhexylorthosilicate is used in a component separator 44 whereas a 20% triethylhexylorthosilicate coating is used in the component separator 46. The carrier gas lines 40 and 42 are connected in common to an input carrier gas supply source 66 preferably of hydrogen and to a common output detection system 50 consisting of an emission source 26', and optical wavelength selector 28', a detector 30' and a recording device 32' with the primed numerical designation intended to emphasize their direct correspondence with their counterpart in FIG. 1.

The hydrogen carrier gas is supplied through a shut-off valve 67 at a regulated pressure and controlled flow rate through each carrier line 40 and 42 respectively. For the samples taken in the recording of FIGS. 8–11 inclusive, the pressure was held at 10 psig and the carrier gas flow rate at 40 ml/min. The sample injectors 60 and 62 are conventional pneumatically operated sliding plate valves which are shown diagrammatically in FIG. 7 for purposes of simplicity. Each sample injector valve includes the port locations designated 1–10 and 1'–10' respectively. The port locations are interconnected to form either one of two flow paths depending upon the state of actuation of the sample injectors. The solid lines between the port locations represent the normal or unactivated flow path whereas the dotted lines represent the actuated flow path. In operation, the carrier gas is constantly flowing through both of the carrier lines 40 and 42 respectively. The carrier gas flows through the sample injectors 60 and 62 either directly from ports 3 to 4 and 3' to 4' or indirectly from the port locations 3 and 3' following the dotted line path through the transfer loops 70 and 70' and then through the sample loops 72 and 72', exiting from port locations 4 and 4' respectively as will be more fully explained hereafter. In the unactivated mode a test gas sample in introduced to the sample injector 60 for detection of $Fe(CO)_5$ at port 9 flowing internally to port 8 through the sample loop 72 to port 5 and internally to port 10. At port 10 the sample exits sample injector 60 and continues to flow to the other sample injector 62 entering at port 9' and flowing internally to port 8' and then through the sample loop 72' to port 5' and finally exiting at port 10' from where the sample gas is vented. The sample gas may flow continuously or intermittently at flow rates up to about 150 ml/min. A sufficient sample volume must be passed through to insure that a representative sample is provided for each analysis.

Beginning a cycle, the $Ni(CO)_4$ sample injector 62 is actuated and the carrier gas is rerouted through the sample injector 62 following the dotted line path from port 3' to port 2', around the transfer loop 70' to port 7', then into port 8' whereby the volume of sample gas contained in the sample loop 72' is pushed by the carrier gas to port 5' from where it flows through port 4' onto the carrier gas line 42 for evaluation. The inject mode is controlled by suitable solenoid valves (not shown) in a conventional manner and is timed to insure that all of the sample in the sample loop 72' is passed onto the carrier gas line 42 for passage through the column 46. The inject mode is then terminated and the sample injector 62 deactivated. The $Fe(CO)_5$ inject valve 60 is then activated and the carrier gas flowing through the carrier gas line 40 rerouted through the sample injector 60 in a manner identical to that just discussed with reference to sample injector 62.

The output from each of the columns 44 and 46 respectively is fed into the output detection system 50. The flame cell 26' also receives a supply of air at about 300–350 ml/min. and at a suitable pressure. The regulated air pressure is adjustable to vary the flow through the cell in order to optimize the oxygen rich flame in the flame cell 26'.

Figure 8:
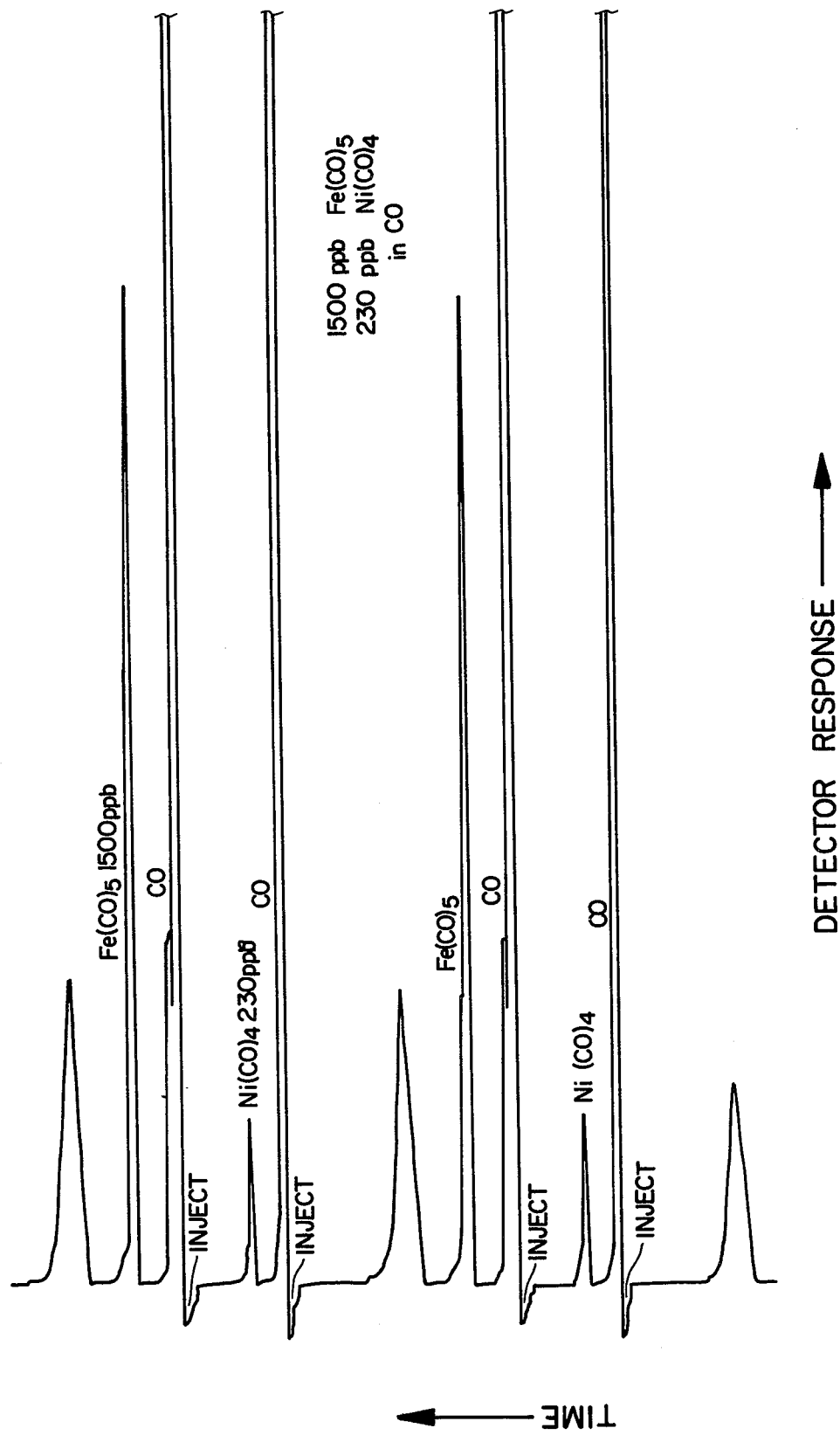
FIG. 8 is a repetitive chromatographic recording of a predetermined sample of iron and nickel carbonyl in a controlled fluid matrix of carbon monoxide in accordance with the present invention.
Figure 9:
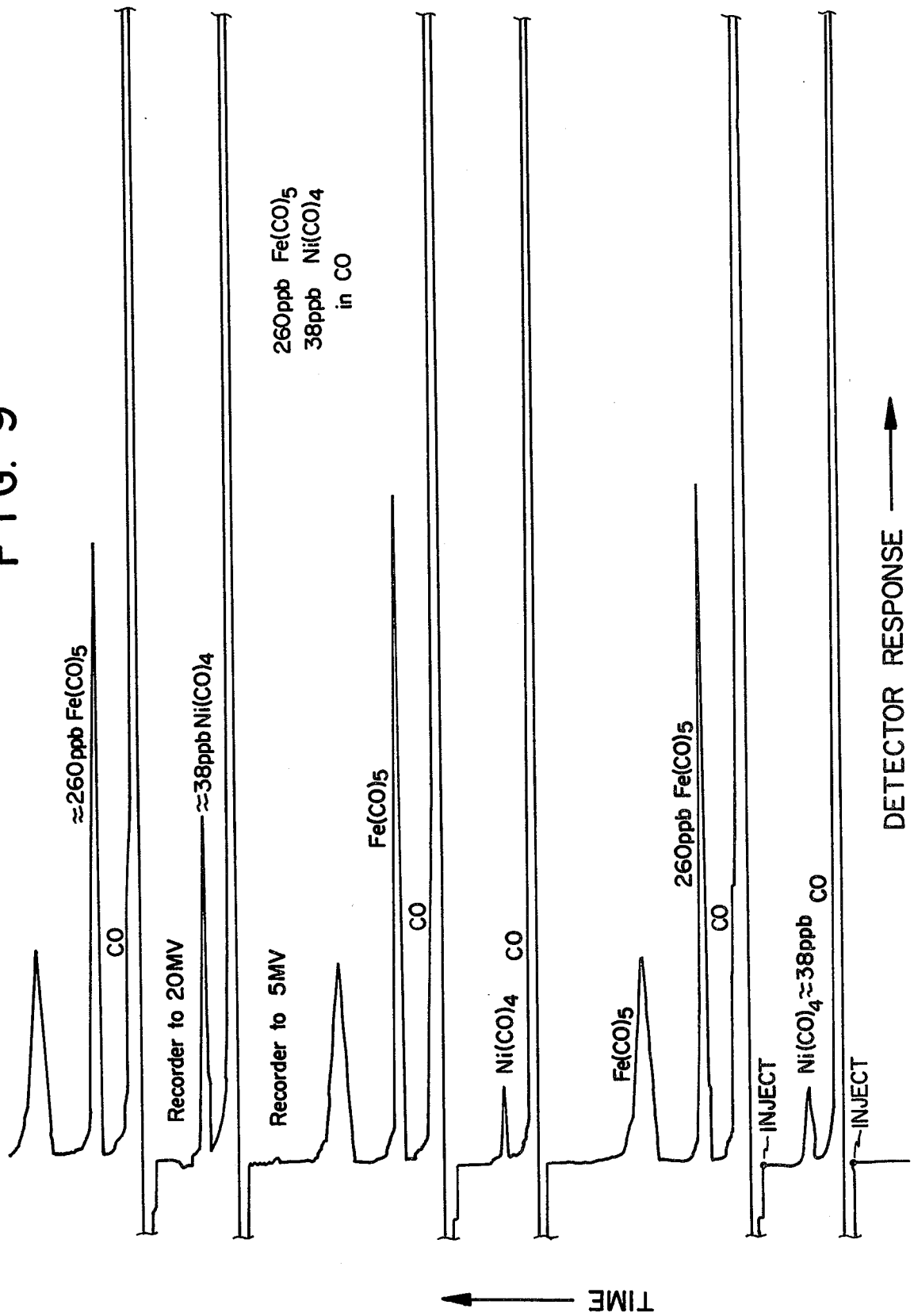
FIG. 9 is another example of a repetitive chromatographic recording similar to that of FIG. 8 for different levels of iron and nickel carbonyl.
Figure 10:
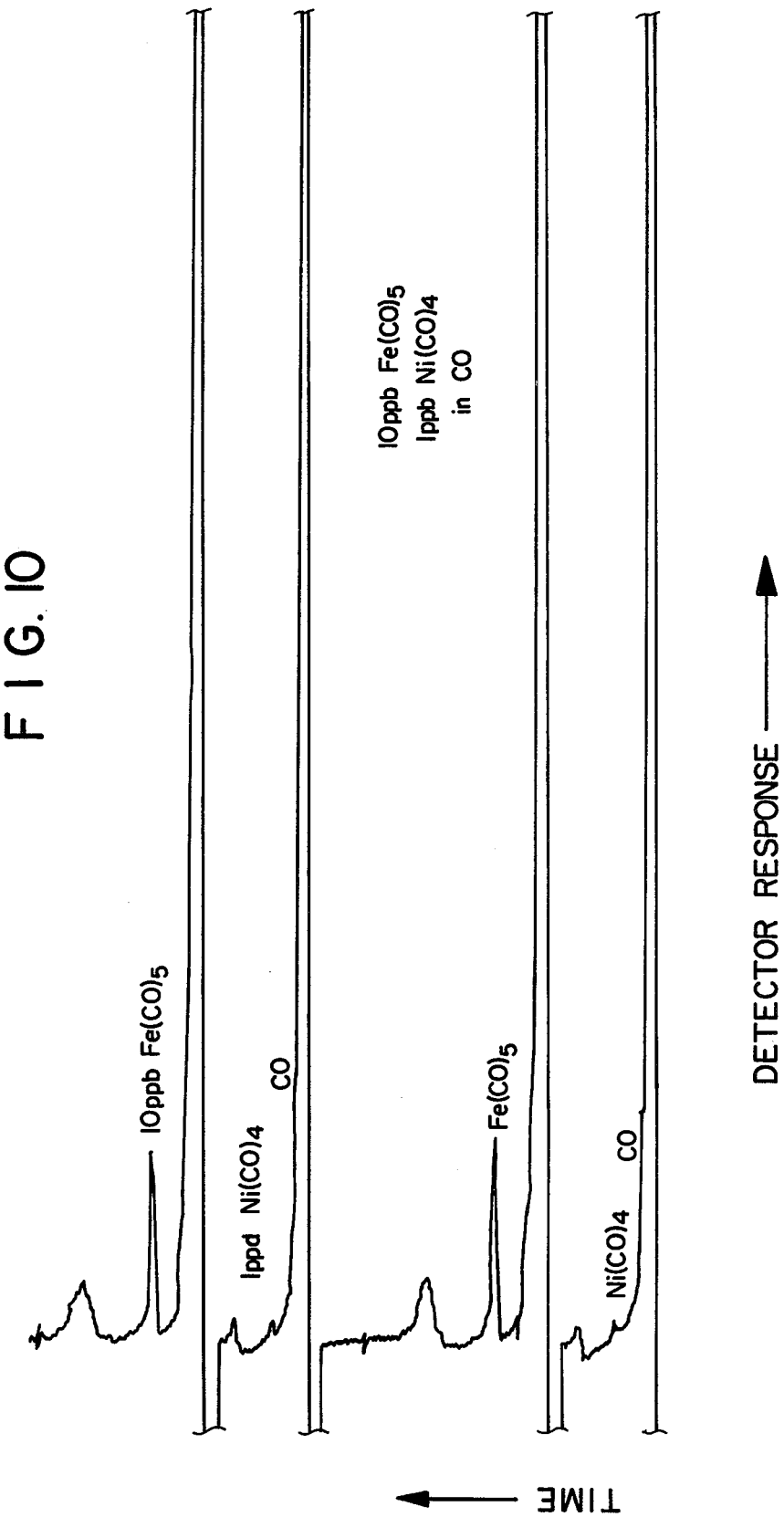
FIG. 10 is yet another example chromatographic recording similar to that of FIGS. 8 and 9 at very low ultra trace levels of iron and nickel carbonyl.

Using the system illustrated in FIG. 7 and under the operating conditions as described in connection therewith a number of chromatographic recordings were taken to analyze for iron pentacarbonyl and nickel tetracarbonyl in sample fluid matrices of carbon monoxide and air respectively. It should once again be emphasized that the particular sample fluid matrix under examination is not critical to the system and accordingly, any fluid matrix may be tested using the method and system of the present invention. FIGS. 8–10 are recorded chromatograms showing different concentration levels of iron pentacarbonyl and nickel tetracarbonyl in a carbon monoxide sample. In FIG. 8 the concentration level of $Fe(CO)_5$ is 1500 parts per billion and the concentration level of $Ni(CO)_4$ is 230 parts per billion. The reading is shown taken from right to left with the CO component eluding first followed by the $Ni(CO)_4$ component. The chromatographic column 46 is tailored to retain the $Ni(CO)_4$ component long enough for the recording to complete the CO detection. The $Fe(CO)_5$ introduced by this injection will elude later as a somewhat broad peak. In the meantime, the other $Fe(CO)_5$ sample injector valve 60 is actuated and a further predetermined volume of sample is introduced into the column 44 tailored to optimize separation and detection of $Fe(CO)_5$. From this column, the $Ni(CO)_4$ component elutes with the CO component. Elution and the detection of the prime $Fe(CO)_5$ peak is achieved prior to elution of the $Fe(CO)_5$ component from the $Ni(CO)_4$ column 46. In FIG. 9 the concentration level of the $Fe(CO)_5$ component is 260 parts per billion and the concentration level for the $Ni(CO)_4$ component is 38 parts per billion. Here again the recording is read from right to left with the CO component producing an off scale signal followed first by a $Ni(CO)_4$ component and then following a second injection by another CO component followed by the $Fe(CO)_5$ component. FIG. 10 is a third example of the detection of iron pentacarbonyl and nickel tetracarbonyl in a carbon dioxide fluid matrix at very low ultra trace concentration level down to 1 part per billion. The nickel tetracarbonyl component was measured at a concentration level of only 1 part per billion and the iron pentacarbonyl at a concentration level of only 10 parts per billion respectively.

Figure 11:
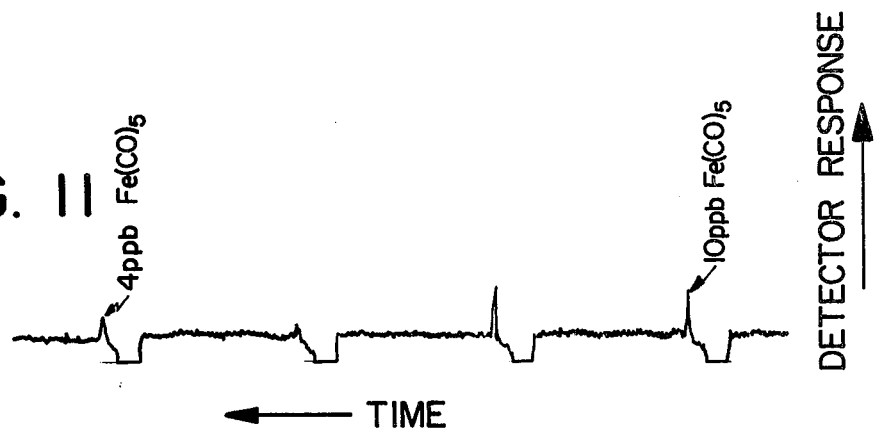
FIG. 11 is a further example chromatographic recording in accordance with the present invention of the spectral emission of a predetermined sample of air.
Figure 12:
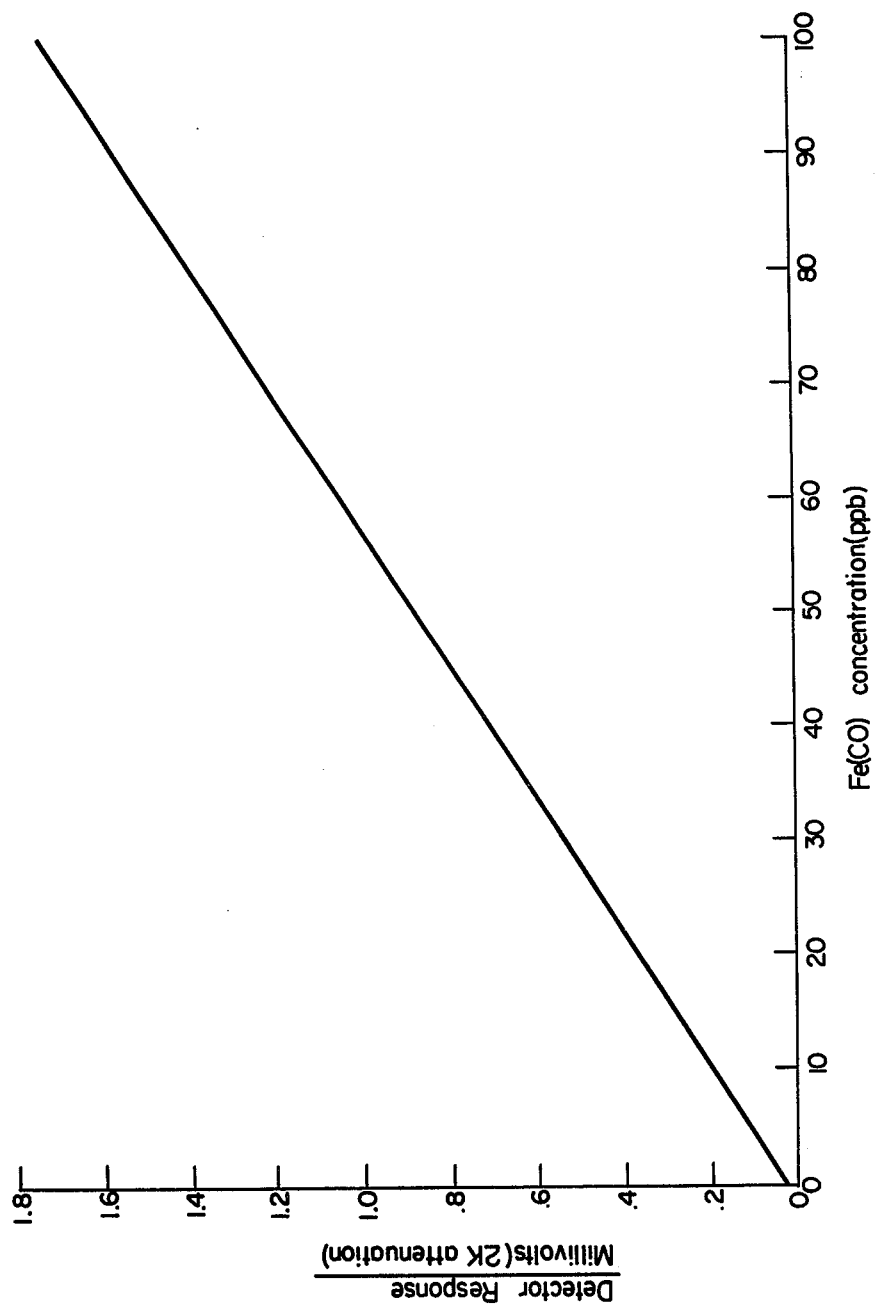
FIG. 12 is a graph illustrating the linearity of detection for iron carbonyl.

A recorded chromatogram of a fluid matrix sample of air is shown in FIG. 11 with the iron carbonyl component measured at 4 and 10 parts per billion. FIG. 12 shows that the concentration level of $Fe(CO)_5$ is linearly related to the recording intensity of levels below 100 parts per billion.

Although the invention has been described with reference to the detection of iron pentacarbonyl $Fe(CO)_5$ and nickel tetracarbonyl $Ni(CO)_4$ respectively, it should be apparent that the method and system of the present invention is equally applicable to the detection of other metal carbonyls simply by the selection of a chromatographic column for the particular metal carbonyl to be analyzed. Other carbonyls that could be detected with the flame emission gas chromatographic analyzer of the present invention would be: $V(CO)_6$, $Cr(CO)_6$, $Mo(CO)_6$, $W(CO)_6$, $Mn_2(CO)_{10}$, $Re_2(CO)_{10}$, $Fe_2(CO)_9$, $Fe_3(CO)_{12}$, $Co_2(CO)_8$, $Ru(CO)_5$, $Ru_2(CO)_9$, $Ru_3(CO)_{12}$, $Os(CO)_5$, $Os_2(CO)_9$, $Rh_2(CO)_8$, $[Rh(CO)_3]_n$, $[Rh_4(CO)_{11}]_n$.

What is claimed is:

1. A method for detecting ultra trace levels of at least one predetermined metal carbonyl within a fluid matrix comprising the steps of:
   (a) sampling said fluid matrix to provide a fluid sample of predetermined volume;
   (b) passing said fluid sample together with a carrier gas through a component separator for separating said predetermined metal carbonyl from the other components in said fluid sample;
   (c) forming a binary admixture between the separated metal carbonyl component and said carrier gas;
   (d) oxidizing said binary admixture in an oxygen rich flame such that a molecular wavelength emission spectrum is generated for said admixture;
   (e) optically selecting a predetermined range of wavelengths in the ultraviolet to visible light region of said emission spectrum from between 350 to 625 nanometers inclusive;
   (f) electro-optically detecting said predetermined range of wavelengths; and
   (g) indicating said detected range.

2. A method as defined in claim 1 wherein said metal carbonyl is selected from the group consisting of $Fe(CO)_5$, $Ni(CO)_4$, $V(CO)_6$, $Cr(CO)_6$, $Mo(CO)_6$, $W(CO)_6$, $Mn_2(CO)_{10}$, $Re_2(CO)_{10}$, $Fe_2(C)_9$, $Fe_3(CO)_{12}$, $Co_2(CO)_8$, $Ru(CO)_5$, $Ru_2(CO)_9$, $Ru_3(CO)_{12}$, $Os(CO)_5$, $Os_2(CO)_9$, $RH_2(CO)_8$, $[Rh(CO)_3]n$, $[Rh_4(CO)_{11}]n$, $Ir_2(CO)_8$ and $[Ir(CO)_3]n$.

3. A method as defined in claim 2 wherein said fluid matrix comprises carbon monoxide.

4. A method as defined in claim 3 wherein said metal carbonyl consists of iron pentacarbonyl or nickle tetracarbonyl.

5. A method as defined in claim 4 further comprising maintaining the spectral bandwidth of said selected predetermined range of wavelengths to no more than about 100 nanometers.

6. A method as defined in claim 5 wherein the wavelength transmission peak of said selected predetermined range of wavelengths should lie within a range of from between about 350 to 400 nanometers.

7. A method as defined in claim 5 wherein the wavelength transmission peak of said selected predetermined range of wavelengths should lie within a range of from between about 500 to 600 nanometers.

8. A method as defined in claim 7 wherein said oxygen rich flame comprises a mixture of fuel and air in a ratio of at least three parts air to one part fuel.

9. A method as defined in claim 2 wherein said fluid matrix comprises air.

10. A system for detecting ultra trace levels of at least two separate metal carbonyls within a given fluid matrix comprising:
   (a) at least a first and second conduit means connected in a parallel relationship;
   (b) means for simultaneously introducing a supply of inert carrier gas from a common source through each of said conduit means at a predetermined pressure and flow rate;
   (c) means for injecting a first gas sample of said fluid matrix into said first conduit means at a first predetermined time interval;
   (d) means for injecting a second gas sample of said fluid matrix into said second conduit means at a second predetermined interval of time;
   (e) first separating means connected in series with said first conduit means for resolving the gas in said first conduit means into a first series of binary admixtures between each of the components of said first fluid matrix sample and said carrier gas;
   (f) second separating means connected in series with said second conduit means for resolving the gas in said second conduit means into a second series of binary admixtures between each of the components of said second fluid matrix sample and said carrier gas;
   (g) means for introducing said first and second series of binary admixtures in common through a flame cell;
   (h) means for maintaining an oxygen rich atmosphere within said flame cell;
   (i) means for filtering the emission spectrum generated from said flame cell such that only a narrow predetermined range of wavelengths from between 350 to 625 nanometer is permitted to pass therethrough; and (j) means for detecting said range of wavelengths.

11. A system as defined in claim 10 wherein said fluid matrix comprises carbon monoxide.

12. A system as defined in claim 11 wherein said separate metal carbonyls are selected from the group consisting of $Fe(CO)_5$, $Ni(CO)_4$, $V(CO)_6$, $Cr(CO)_6$, $Mo(CO)_6$, $W(CO)_6$, $Mn_2(CO)_{10}$, $Re_2(CO)_{10}$, $Fe_2(CO)_9$, $Fe_3(CO)_{12}$, $CO_2(CO)_8$, $Ru(CO)_5$, $Ru_2(CO)_9$, $Ru_3(CO)_{12}$, $Os(CO)_5$, $Os_2(CO)_8$, $[Rh(CO)_3]n$, $[Rh_4(CO)_{11}]n$, $Ir_2(CO)_8$ and $[Ir(CO)_3]n$ 13. A system as defined in claim 12 wherein said first and second separating means each comprise a chromatographic column including a packing material of chromasorb P coated with triethylhexylorothosilicate.

14. A system as defined in claim 13 wherein said first separating means has a 5% coating of triethylhexylorothosilicate for specifically detecting iron pentacarbonyl and wherein said second separating means has a 20% coating of triethylhexylorothosilicate for specifically detecting nickel tetracarbonyl.

* * * * *